(12) United States Patent
Fleischer

(10) Patent No.: US 7,637,894 B2
(45) Date of Patent: Dec. 29, 2009

(54) PLASTER DEVICE

(75) Inventor: Philip Fleischer, Copenhagen (DK)

(73) Assignee: Lina Medical ApS, Glostrup (DK)

( * ) Notice: Subject to any disclaimer, the term of this patent is extended or adjusted under 35 U.S.C. 154(b) by 33 days.

(21) Appl. No.: 11/913,639

(22) PCT Filed: May 5, 2006

(86) PCT No.: PCT/IB2006/051417

§ 371 (c)(1),
(2), (4) Date: Apr. 25, 2008

(87) PCT Pub. No.: WO2006/120623

PCT Pub. Date: Nov. 16, 2006

(65) Prior Publication Data

US 2008/0221526 A1    Sep. 11, 2008

(30) Foreign Application Priority Data

May 6, 2005    (DK) ................................ 2005 00665

(51) Int. Cl.
*A61M 5/32* (2006.01)
(52) U.S. Cl. ..................... 604/174; 604/180
(58) Field of Classification Search ......... 604/174–180, 604/530; 128/DIG. 26
See application file for complete search history.

(56) References Cited

U.S. PATENT DOCUMENTS

| | | | | |
|---|---|---|---|---|
| 4,360,025 A * | 11/1982 | Edwards | .................. | 604/180 |
| 4,699,616 A * | 10/1987 | Nowak et al. | ............... | 604/180 |
| 4,986,815 A | 1/1991 | Schneider | .................. | 604/180 |
| 5,215,532 A | 6/1993 | Atkinson | .................. | 604/180 |
| 5,370,627 A * | 12/1994 | Conway | .................. | 604/180 |
| 5,681,290 A * | 10/1997 | Alexander | .................. | 604/180 |
| 5,738,661 A * | 4/1998 | Larice | .................. | 604/180 |
| 6,231,547 B1 * | 5/2001 | O'Hara | .................. | 604/174 |
| 6,273,873 B1 * | 8/2001 | Fleischer | .................. | 604/174 |
| 6,387,076 B1 * | 5/2002 | Landuyt | .................. | 604/174 |
| 6,572,588 B1 * | 6/2003 | Bierman et al. | ............. | 604/180 |

FOREIGN PATENT DOCUMENTS

| | | |
|---|---|---|
| EP | 432 880 A2 | 6/1991 |
| EP | 0574 961 A1 | 12/1993 |
| GB | 2 288 538 A | 10/1995 |
| WO | WO 99/59671 | 11/1999 |

* cited by examiner

*Primary Examiner*—Matthew F Desanto
(74) *Attorney, Agent, or Firm*—Winston & Strawn LLP

(57) ABSTRACT

A plaster device serves for fixating a length of a medical tube in relation to a skin surface of an individual having the tube inserted into a body part via an access opening. The plaster device includes an adhesive part having an upper side an adherent lower side for attaching the device to the skin, and a through-opening for receiving the tube. A support part is provided on the upper side of the adhesive part and arranged for supporting an inserted tube at a bent section. The support part is partly joined to the adhesive part and includes first and second oppositely facing jaws for taking hold of at least a section of the bent tube. The jaws are interconnected at oppositely facing first ends by a support section arranged adjacent to the through-opening in the adhesive part.

15 Claims, 6 Drawing Sheets

PLASTER DEVICE

Figure 1:
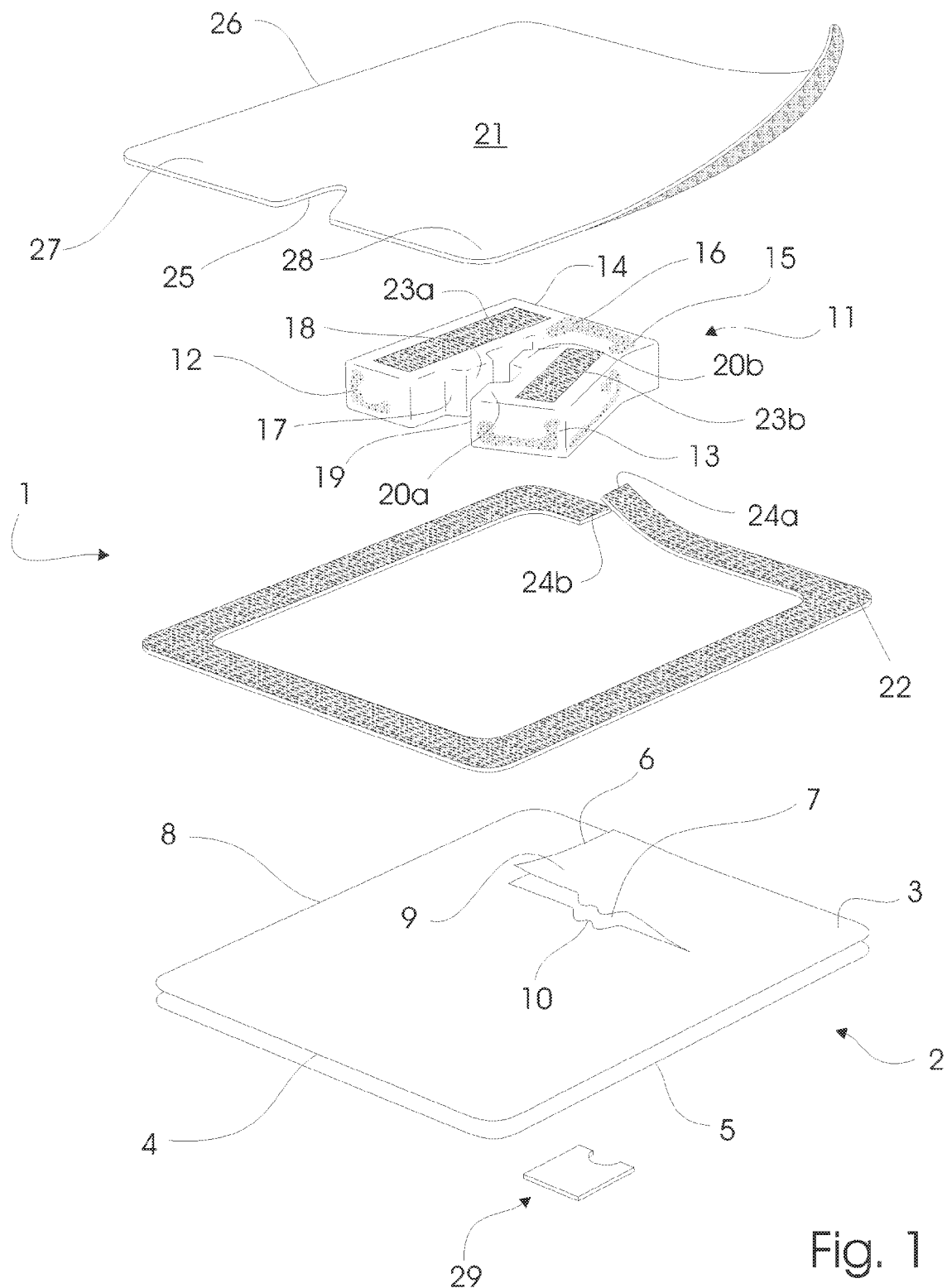

The present invention relates to a plaster device for fixating a length of a medical tube in relation to a skin surface of an individual having said tube inserted into a body part via an access opening.

The plaster device is of the kind that includes an adhesive part having an upper side, an adherent lower side for attaching the plaster device to the skin, and a through-opening for receiving the tube, and a support part provided on the upper side of the adhesive part and arranged for supporting an inserted tube at a bent section.

Medical tubes are often introduced into a wound, a vessel, a cavity or an organ of a human or animal body to facilitate sustained drainage or sustained supply of liquid or gaseous substances.

Examples of medical tubes used for drainage include, but are not limited to, a chest drainage tube, a lumpectomy or a mastectomy drainage tube, a renal drainage tube for use in e.g. dialysis or percutaneous nephrostomy, and a drainage tube for emptying e.g. an encystment or an abscess.

Examples of medical tubes used for supplying a substance to the patient include, but are not limited to, tubes and catheters for controlled administration of palliatives, such as analgesia, and hormones, such as insulin, delivered via e.g. an insulin pump.

It is of outmost importance to avoid contamination of the incision site and to avoid dislodgement of the tube, e.g. during inspection of the incision site or during the patient moving, and to avoid kinking, blocking or obstruction of the tube to prevent discontinuity of drainage or supply.

Accordingly, proper securing of the medical tube at and in relation to the patient's skin is necessary to improve the patient's comfort during the treatment.

Traditionally, a medical tube inserted into the patient through an incision in the skin is fixated by means of sutures at the incision site. Such sutures leave scars and may even serve as wicks for undesirable contamination of the incision and the skin around the incision site. To prevent such contamination and to improve securing of the tube, a plaster strapping can be attached to both the skin and around the tube adjacent the incision.

Several approaches have been made to improve this securing technique, which is very distressing to the patient. Nowadays, more sophisticated techniques are used due to improved plaster devices and skin-friendly adhesives.

An improved catheter retainer has been suggested in British patent document GB 2,288,530. The retainer can be adhesively secured to a patient's skin at the incision site to hold an introduced catheter in a fixed position. The retainer allows the catheter to be bent through a right angle as the catheter exits the patient without it kinking. The catheter is kept in place in the bent position in a slot by means of a clamp which compresses and clamps the catheter into the slot. This device has uncomfortable, rigid parts protruding from the patient's skin and the patient's clothes may be caught on the clamp which accordingly will release the catheter. Another disadvantage is that it is impossible to inspect the incision site and consequently it is impossible to obtain information regarding infection at the site and/or leakage through the incision.

A plaster device without any substantially rigid parts is known from International patent application WO 95/33508. A tube is supported on a support component such that the tube changes orientation from an orientation substantially perpendicular to the patient's skin to an orientation substantially parallel to the patient's skin. The tube is fixated in this bent use position by means of an adhesive securing strip applied sealingly over the tube and the support component. The incision site is inspectable only if the adherent securing strip is transparent. If the strip is removed for further inspection, this manipulation may displace the tube resulting in discomfort for the patient. In addition, the tube is covered with adhesive residues and will inadvertently stick to any adjacent component. Due to this disadvantage, the nurse is not inclined to perform as many inspections as are needed in order to be completely sure that e.g. no bleeding, infection or allergic reaction appears around the incision site, of which a part is hidden by the bent tube.

A groove, which is provided in the support part, serves for preventing sidewise displacement of the tube. The size of the groove limits the diameter of the tube, and longitudinal displacement is difficult to avoid if the diameter of the tube is less than the width of the groove. A securing strap is intended for holding the tube in place in the groove, however this solution involves a risk that the tube will be dislocated or squeezed when the strap is tightened.

It is a first aspect according to the present invention to provide a simple and inexpensive plaster device for improved fixation on a patient's skin of a medical drainage or supply tube.

It is a second aspect according to the present invention to provide a plaster device for fixating a medical drainage or supply tube on a patient's skin in a position of use, in which kinking, blocking, compressing or obstruction of the tube is prevented.

It is a third aspect according to the present invention to provide a plaster device which is easy to apply and use, and provides a comfortable and convenient fixation of a medical drainage or supply tube on a patient's skin.

It is a fourth aspect according to the present invention to provide a plaster device which does not get caught in the surroundings, e.g. the patient's clothes.

It is a fifth aspect according to the present invention to provide a plaster device for preventing a medical drainage or supply tube inserted through a patient's skin from displacement and dislocation after fixation and during movement of the patient.

The novel and unique feature whereby this is obtained is the fact that the support part is partly joined to the adhesive part and comprises first and second oppositely facing jaws for, in between them, taking hold of at least a section of the bent tube.

A medical tube, which is carefully inserted via an access opening in the skin surface and placed at a selected location into a vessel or a body cavity, must be bent back towards the skin surface and fixated to said surface in order to ensure, that the position of the tube are properly secured at the access opening and that the tube does not does not get caught in the surroundings.

The risk of the tube kinking during this bending is prevented if the jaws are interconnected at oppositely facing first ends by means of a support section. The support section provides support for the proximal bent section of the inserted tube, that is the section of the tube which is in close proximity to the access opening in the skin surface.

In order to improve and perfect this anti-kinking property, the support section may have, seen in cross-section, a raised curvature for guiding the bent tube through a smooth curve of a radius sufficiently large to prevent kinking and compression of the bent tube section.

The through-opening of the adhesive part of the plaster device is situated superjacent to the access opening in the skin surface of a patient so as immediate support for the inserted tube is provided.

Having been passed carefully over the support section, the distal part of the bent tube is passed further in between the co-operating fist and send jaws, preferably complementarily shaped jaws, to be placed and retained between these oppositely facing jaws in order to obtain optimum hold of the inserted tube.

Said hold of the inserted tube can be further improved if at least one of the inside walls is provided with an adhesive. Optionally the adhesive on the inside wall is covered with a detachable protective strip of foil, to be removed just before the tube is bent and placed between the jaws. The adhesive provides a means for keeping the tube free of contact with the subjacent adhesive part and thereby minimise the patient's considerable inconvenience of having a tube inserted in and fixed to the body.

To further prevent the bent length of the tube from dislodging from the plaster device can comprise a retainer plate for holding down the proximal bent length of the tube interposed between the two opposite facing first and second jaws. At least a part of the retainer plate can be permanently secured to the upper side of the support part e.g. by means of an adhesive.

In contrast to prior art plaster devices the plaster devices according to the present invention can, due to the variable distance between the jaws, retain tubes of many different diameters.

By using the plaster device according to the invention, dislocation and dislodging of the tube in the access opening can be avoided.

The support section can be permanently joined to the upper side of the adhesive part, e.g. by means of an adhesive, adjacent to the through-opening in the adhesive part to be in proper position for supporting the proximal section of the inserted tube during bending.

In order to distribute the compressive forces of the bent tube over the entire support section, it is preferred that the centre of the support section is arranged adjacent to the through-opening in the adhesive part, symmetrically in relation to this through-opening.

The jaws may be pivotably connected to an end of the support section so that the distance between said jaws can be adjusted according to the required need and tube in question.

A cover means can advantageously be provided for protecting the inserted tube, which rests secured on the support section of the plaster device.

In a preferred embodiment the cover means include a first cover part arranged for coupling together with either a second cover part attached to at least a section of the upper side of the adhesive part or for coupling to the adhesive part itself.

The risk of infection is considerably reduced because the first and second cover parts, when joined together, completely enclose the entire support part, the supported bent length of the tube and the incision site.

In a first very simple preferred embodiment the first cover part is an at least partly detachable sheet of textile, preferably entirely made of a VELCRO® hook and loop fastener or made of a textile having a VELCRO® hook and loop fastener strip provided along the perimeter. It is preferred that the sheet has an area sufficiently large to cover at least the support part in the use position and that the textile is air permeable so that humidity is allowed to evaporate and humidification is avoided.

The VELCRO® hook and loop fastener sheet can be fully detachable or can be connected to e.g. an edge or rim portion of the adhesive part.

In this first simple embodiment the second cover part for coupling together with the first cover part can be an annular VELCRO® hook and loop fastener strip attached to the upper side of the adhesive part along or a small distance from the perimeter of this, and arranged for sticking to the first cover part. A preferred distance between the perimeter of the adhesive part and the outline of the second cover part could for example be between 1-5 mm. This distance guarantees that the adhesive part does not detaches the skin to which the adhesive part is attached when the first cover part from time to time is removed for inspection of the tube or access opening.

Either the side of the rim portion of the first cover part facing the adhesive part or the rim portion of the upper side of the adhesive part itself or both these portions may, for some purposes, be glued in order to stick sealingly together.

For some applications a second embodiment according to the present invention may be more preferred. In this second embodiment a section of a first cover part is inserted between the upper side of the adhesive part and the lower side of the support part and joined to both parts, e.g by gluing. A free section of the first cover part emanates from underneath the support part. As a result of this design, at the same time as the free section of the first cover part are brought to cover the support part, the jaws will be drawn towards each other to carefully fixate the tube inbetween them. Accordingly, in one single procedure the bent length of the tube is both covered and anchored.

This procedure is especially easy to carry out if the second cover part is at least one VELCRO® hook and loop fastener strip attached to the upper side of the adhesive part adjacent at least a part of the outer face of the support part along the perimeter of the part.

The free section of the first cover part can advantageously be provided with a number of protruding flaps for engaging with the at least one sized VELCRO® hook and loop fastener strips of the second cover part. In the position of use two adjoining flaps define the exit direction for the proximal bent length of the tube, which is covered by the first cover part. For enabling easy inspection of the tube the first cover part can also be designed with a detachment flap.

It is preferred that the first cover part in the form of a VELCRO® hook and loop fastener sheet has a smooth outside so that the plaster device not does catch the patient's clothes or other surrounding protruding elements.

A third cover part, e.g. of the same VELCRO® hook and loop fastener material as the second cover part, can be provided on at least a part of the top face of the support part for engaging with the first cover part in such a way that the retaining grip of the oppositely facing jaws around the tube is maintained. The third cover part can furthermore extend down to the adhesive part joined to the outer side face of a jaw.

In this position of use the first and the third cover part together with the first and second jaws constitute a simple fastening means for the inserted bent length of the tube. Furthermore, the second and the third cover parts are arranged for coupling together with the first cover part to protect and enclose the tube so as to minimise the infection risk.

For enabling easy and correct application of the plaster device on the skin surface close to the incision site and the access opening, the adhesive part may have a slit extending from the outer perimeter of the adhesive part to the through-opening of the adhesive part.

In an advantageous embodiment according to the present invention a pad is inserted between the adhesive part and the support section adjacent to the through-opening in the adhesive part. Such a pad may e.g. serve for absorbing secretions or is impregnated with a substance for slow release delivery of the substance at a location such as the skin surface or the incision site. Within the scope of the present invention the pad may for this purpose comprise at least one of the substances selected from the group including an absorbent agent, a bactericide, a fungicide or a medicament.

To ensure that the pad has sufficient access to the skin area adjacent or around the opening in the body part to fulfil the above mentioned functions, the through-opening has an area which allows a major part of the pad to directly contact the skin surface.

Additional absorbing pads or layers may be added to the structure or inserted where needed. A hydrocolloid is an example of an included absorbent agent, which ensures that the incision site is kept dry. Compositions including e.g. a bactericide, an antibiotic and/or an antifungal agent are able to kill or inhibit any active bacteria or fungus which may be included in the structure or which has contaminated the structure. Any medicament can be included in the structure. The absorbent layers or pads may be of any convenient material known to the person skilled in the art, e.g. cellulose webs, porous pads, non-wovens etc.

A releaseable foil may be included in the plaster device for protecting the adherent lower side of the adhesive part during storage.

It is preferred that the support part is made of a foamed material which is substantially dimensionally stable so that it will essentially keep its shape when the plaster device is used, and is so flexible that it will yield without compressing the supported tube if the patient bumps or presses against something. One preferred material is foamed polyethylen, which is soft and still dimensionally stable.

If the first cover part is removed for inspection of the tube, coupling between the first and second cover part is disengaged and the jaws can be carefully spread so that the tube can be carefully lifted free of the support section. Areas otherwise not inspectable, such as e.g. the incision site hidden between the bent tube and the support section, can now easily be inspected and treated sufficiently early to prevent damages.

If occasion should render it necessary and appropriate, the tube may even be substituted by a new tube without change of the plaster device in use, or the plaster device can be substituted without changing the tube. No or minimal physical adherence exists between the inserted tube and the fastening means and the securing capability is not lost or reduced by simply disengaging the cover parts as with the prior art devices.

Figure 2:
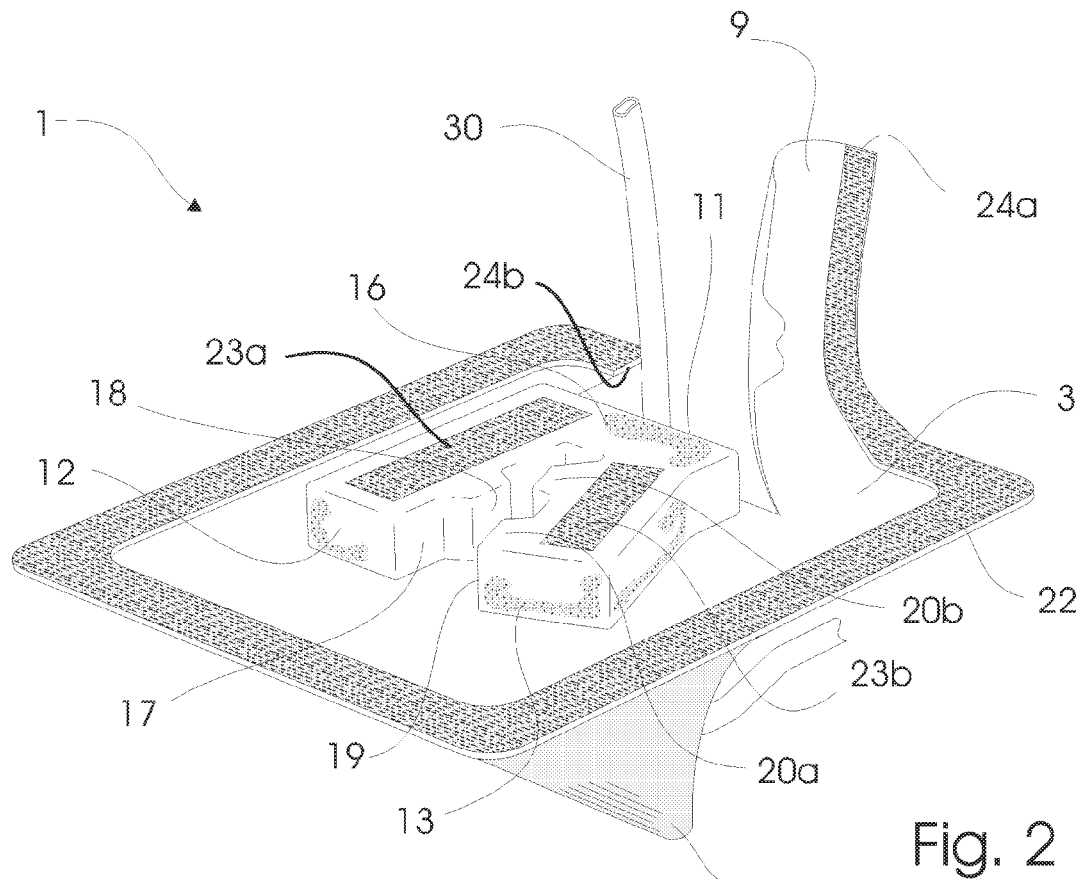
Figure 3:
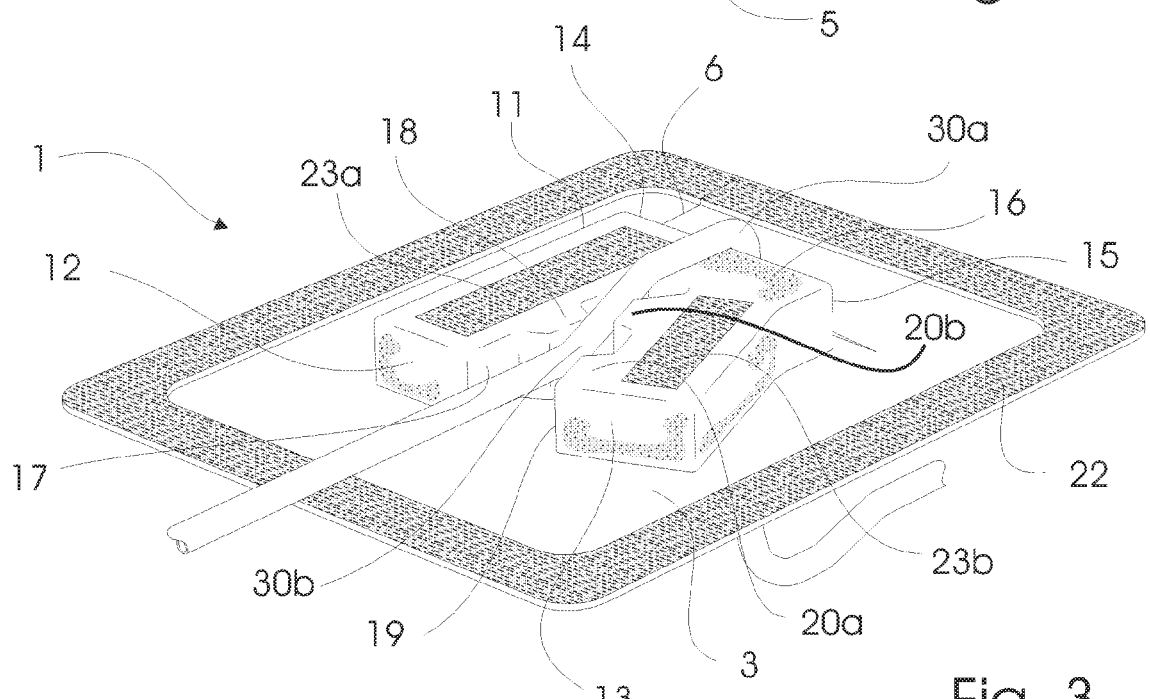
Figure 4:
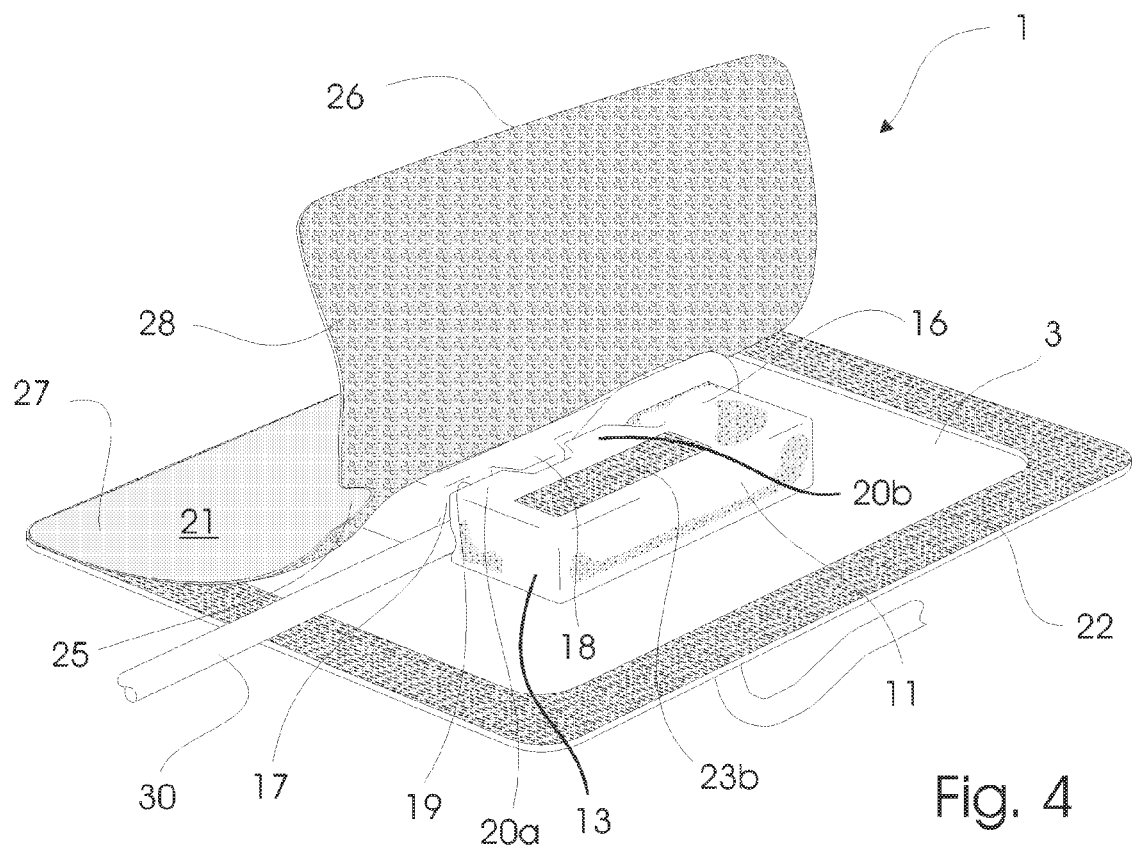
Figure 5:
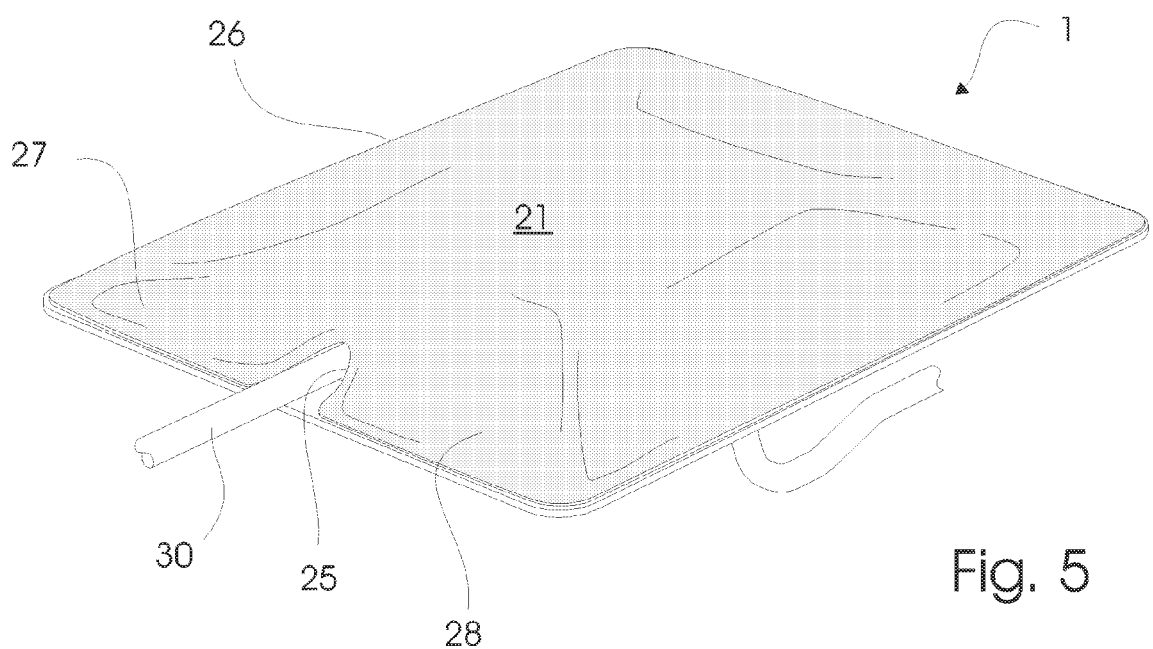
Figure 6:
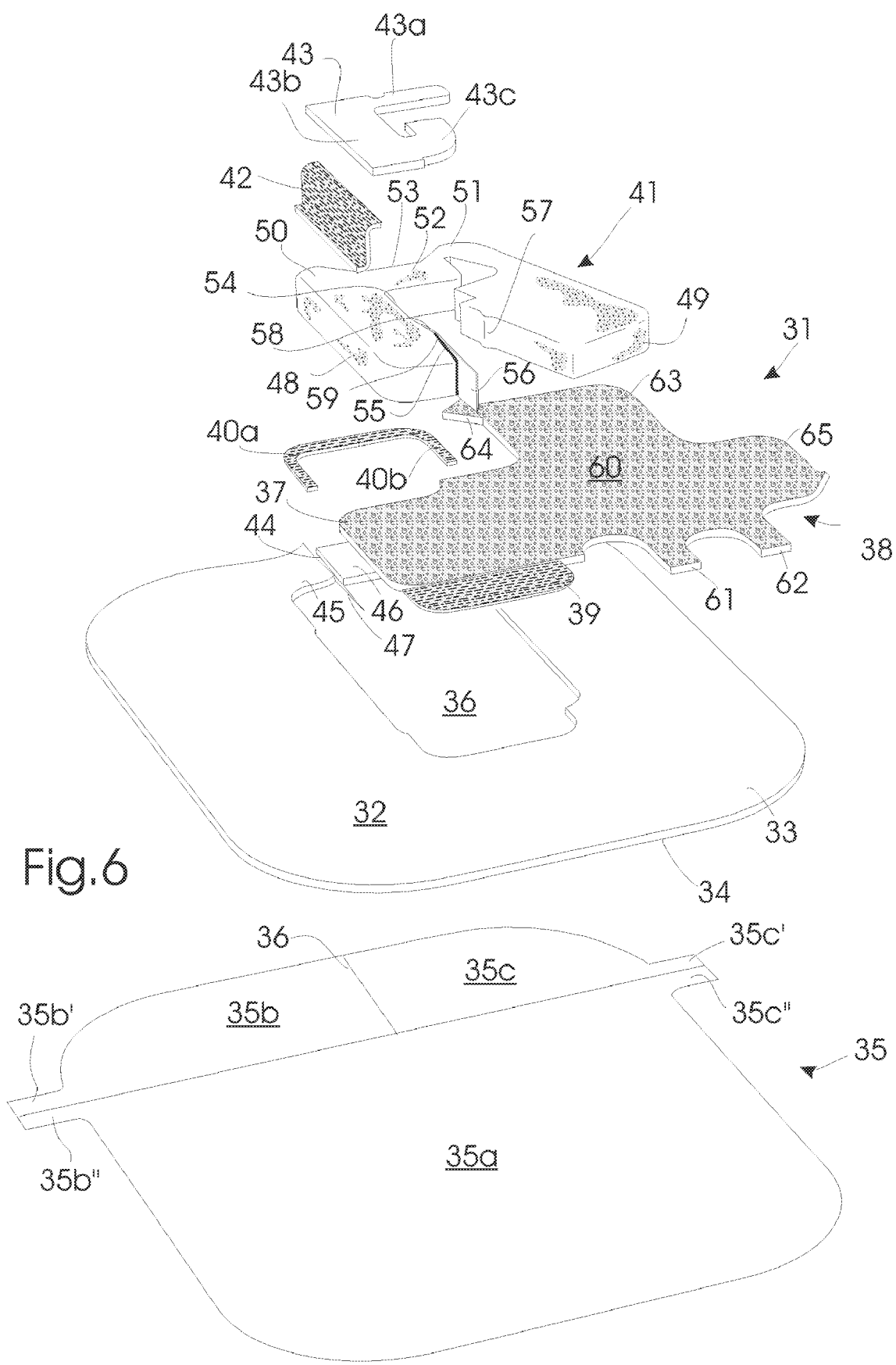
Figure 7:
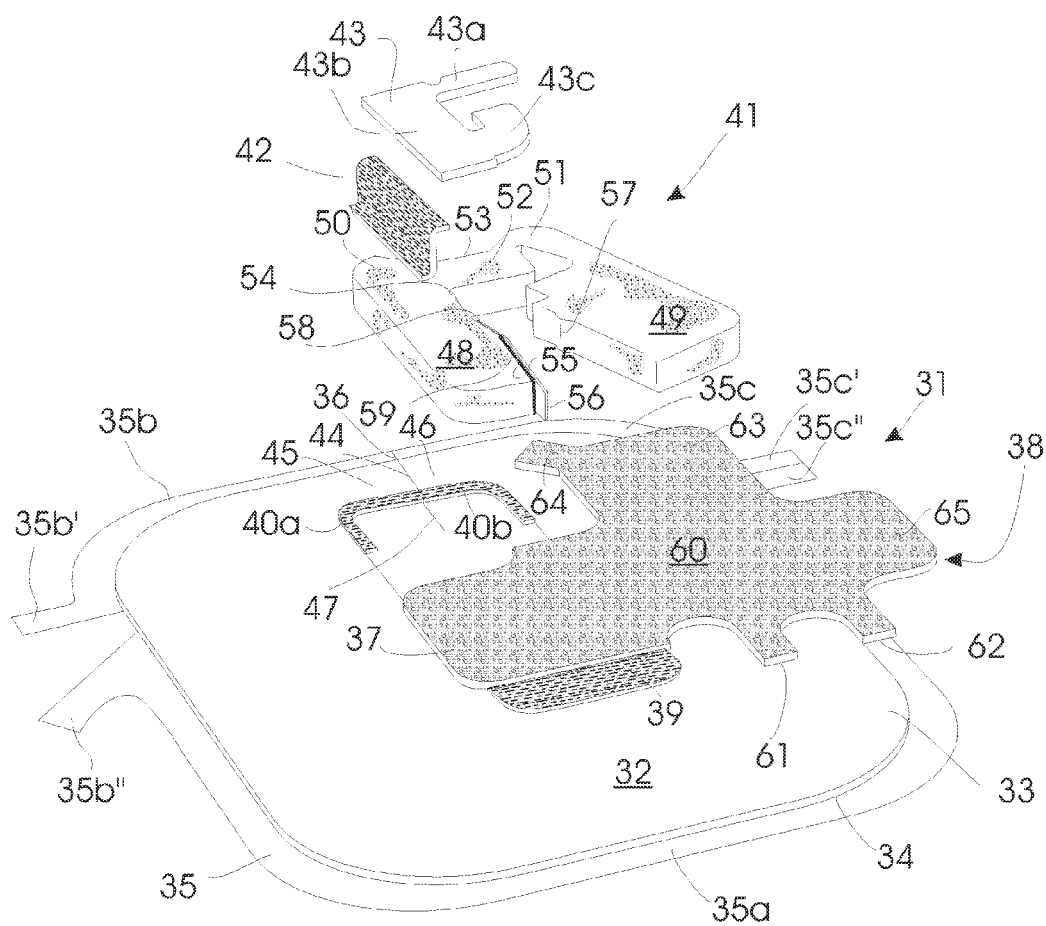
Figure 8:
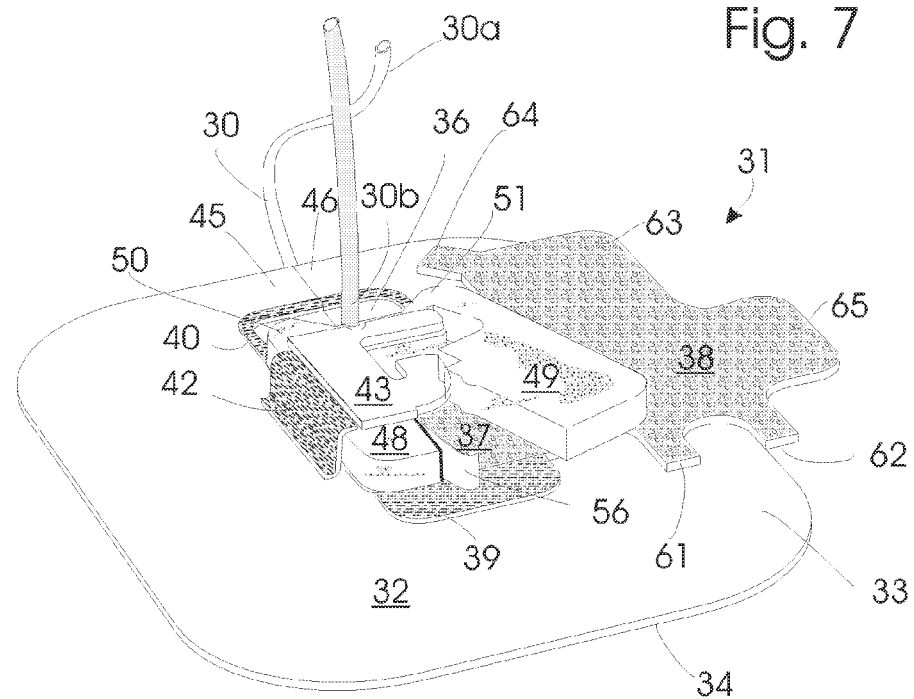
Figure 9:
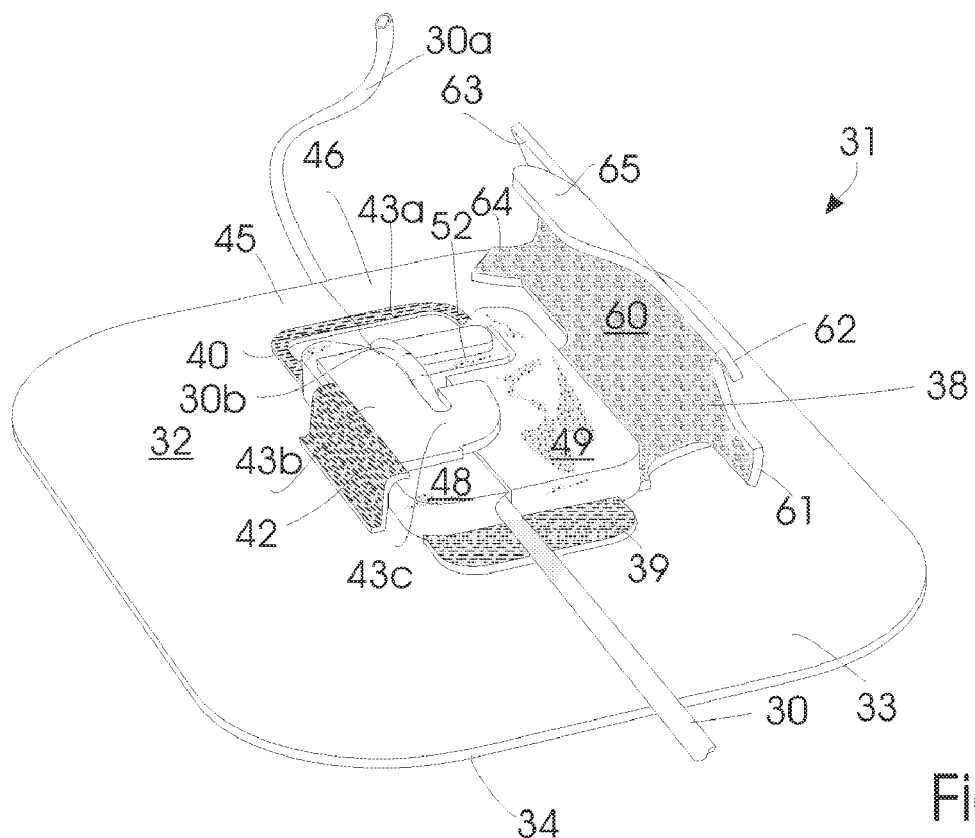
Figure 10:
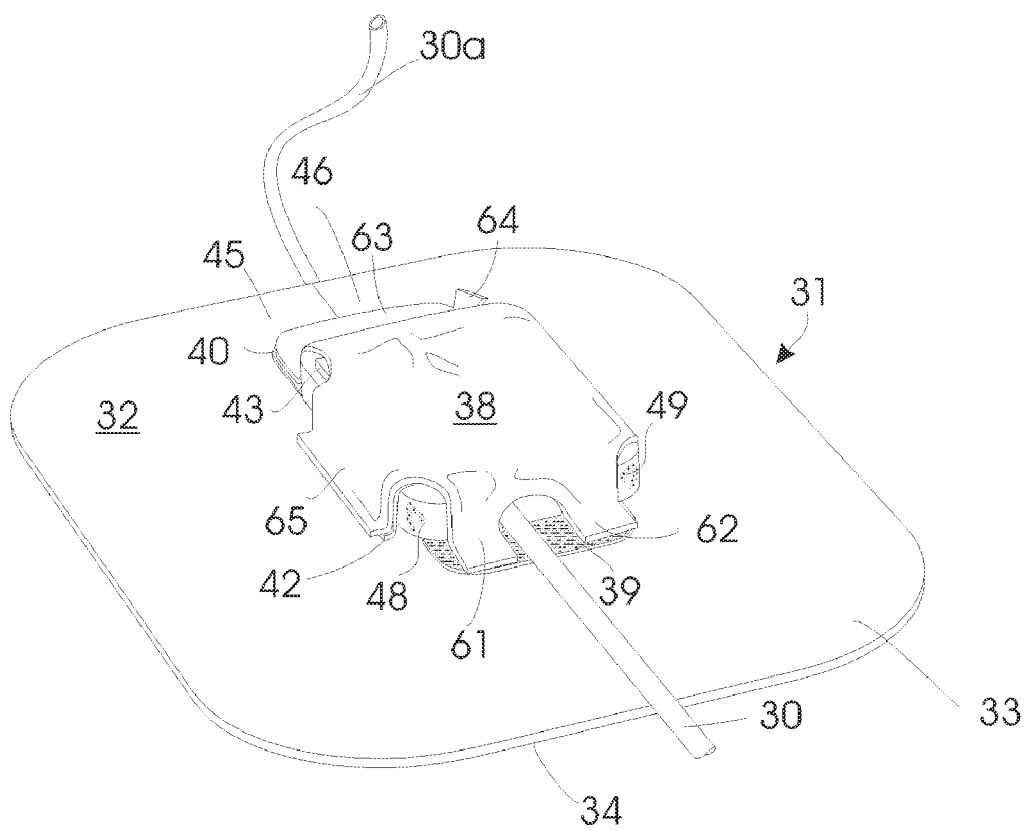

The invention will be further described below with reference to the drawings showing an example of an embodiment for a plaster device according to the present invention, in which FIG. 1 is an exploded view of the elements of a first embodiment of a the plaster device according to the present invention, FIG. 2 shows schematically the plaster device shown in FIG. 1 prepared for application on a skin surface in relation to an inserted tube at a first step of the fixation procedure, FIG. 3 shows schematically the same in a second step of the fixation procedure, in which the tube is bent through a right angle and passed between the spread-apart jaws of the support part, the releaseable foil now being removed, FIG. 4 shows schematically the same in a third step of the fixation procedure, in which the jaws surround a distal part of the bent, inserted tube, and FIG. 5 shows schematically the same in a fourth step of the fixation procedure, in which the first cover part is coupled to the second cover part for enclosing and protecting the bent length of the tube and fastening the tube, FIG. 6 is an exploded view of the elements of a second embodiment of a the plaster device according to the present invention, FIG. 7 shows schematically and partly in an exploded view the second embodiment of the plaster device according to present invention with the adhesive part prepared with first and second cover parts, FIG. 8 shows schematically the same prepared for application on a skin surface in relation to an inserted tube at a first step of the fixation procedure, and where the releasable foil has been removed, FIG. 9 shows schematically the same in a subsequent step of the fixation procedure, in which the tube is bent through a right angle and passed between the jaws of the support part below a retainer plate, FIG. 10 shows schematically the same in a final step of the fixation procedure, in which the first cover part is coupled to the second cover part for enclosing and protecting the bent length of the tube and fastening and anchoring the tube.

A short length of the medical tube is shown in the figures for illustrative purposes only. Although not shown in the figures it should be understood that the plaster devices according to the present invention is applied to the patients skin in relation to an access opening.

It will furthermore be clear to the person skilled in the art that, within the scope of the present invention, other geometrical outlines of the support part and the adhesive part, such as e.g. oval, circular or triangular outlines, are also within the scope of the present invention.

The elements of a first embodiment of a plaster device 1 are shown in the exploded view in FIG. 1.

The plaster device 1 includes an adhesive part 2 having an upper side 3 and an adherent lower side 4 coated with a skin-friendly adhesive. By the term "a skin-friendly adhesive" is understood any medical adhesive commonly used, which is non-allergic, non-irritating and does not provoke massive redness and/or pruritus.

The adhesive is protected by a releasable foil 5 which is removed just before the plaster device is attached to the skin surface (not shown). A slit 6 connects a through-opening 7 in the adhesive part 2 to the perimeter 8 of the adhesive part 2 and divides an access flap 9. Upon application of the plaster device 1 the foil 5 is removed, the access flap 9 is lifted aside, the through-opening 7 is located at the incision site adjacent to the inserted tube, and the lower side 4 of the adhesive part 2 is adhered to the skin of the patient.

In the case shown, the through-opening 7 is a simple zigzag section 10 of the slit 6, however any appropriate geometry of the through-opening, such as a circular cut-out, is within the scope of the present invention. The small jags of the zigzag section can be cut off to enlarge the size of the through-opening or can be adhered to the tube if desired.

A substantially U-shaped support part 11 is joined to the upper side 3 of the adhesive part 2 for supporting an inserted tube at a bent section. The support part 11 is partly joined to the adhesive part 2 and comprises first 12 and second 13 oppositely facing jaws for, in between them, taking hold of at least a section of the bent tube, said jaws 12,13 are interconnected at oppositely facing first ends 14,15, respectively, by a support section 16 arranged adjacent to the through-opening 7 in the adhesive part 2.

The inside wall 17 of the first jaw 12 is formed with protrusions 18 which are complementarily shaped to protrusions 20a,20b formed on the inside wall 19 of the second jaw 13. The resiliency of the foam material of the support part 11 and in particular of the protrusions 18,20a,20b establishes sufficient room for accommodating the tube in between the jaws 12,13 in frictional, non-displaceable engagement without compressing the tube. Any suitable number of protrusions 18,20a,20b are within the scope of the present invention.

The cover means 5 consists of a first cover part 21 and a second cover part 22 and a third cover part 23 joined to the top face of the support part 11 and facing the first cover part 21.

In the case shown, the third cover part 23 is composed of two separate strips 23a,23b firmly attached on the free top faces on each respective jaw 12,13.

The first cover part 21 is, in the embodiment shown in the FIG. 1, a rectangular VELCRO® hook and loop fastener sheet having substantially the same or slightly greater area compared to the adhesive part 2.

It is preferred that the second cover part 22 does not cover the entire adhesive part 2, which preferably is made of a transparent material allowing inspection of the skin surface underneath it. Hence, the second cover part 22 is preferably a rectangular strip 22, also made of VELCRO® hook and loop fastener so as not to cover the entire adhesive part. The VELCRO® hook and loop fastener strip 22 is attached along the perimeter 8 of the adhesive part 2 on the outer rim portion of said adhesive part 2, e.g. by means of an adhesive. The strip 22 faces the first cover part 21. The ends 24a,24b of the strip 22 meet at oppositely facing sides of the slit 6 to allow the access flap 9 to be swung aside. Due to the narrow width of the second cover part 22, a central area of the adhesive part 2 remains uncovered. Inspection of the underlying skin surface is therefore still possible.

The cover parts 21,22,23 can firmly and detachably be joined together by velcroing. Especially, the third cover part 23 engages the first cover part 21 in any position the jaws 12,13 may be placed in.

The cover parts 21,22,23 can have other types of adherent or sticky contact areas, such as e.g. glued contact areas covered by protective peelable foils. However, these alternatives are less preferred since such joinings are difficult to break and re-establish without damaging the adhesiveness of the cover parts or risking that the adhesive part 2 detaches from the skin surface to which the device 1 is attached.

The first cover part 21 has a cover part slit 25 which extends a distance from the perimeter 26 of the first cover part 21 into said first cover part 21. The slit 25 defines two oppositely facing flaps 27,28 which, together with the slit 25, serve for guiding the bent length of the tube free of the plaster device 1 and for holding the tube substantially parallel to the subjacent skin surface (not shown).

A pad 29 is inserted between the adhesive part 2 and the support section 16 adjacent to the through-opening 7 in the adhesive part 2. The pad 29, which is placed in contact with the skin area, is able to absorb secreted body fluids or tissue fluids or is able to deliver a substance, such as a medicament or bactericidal agent to the subjacent skin area.

The elements shown in FIG. 1 are combined to the plaster device 1 as shown in FIG. 2.

In FIG. 2 the protective foil 5 is shown partly detached from the adhesive part. For illustrative purposes a tube 30 is shown traversing the adhesive part 2 via the through-opening 7. The tube 30 is inserted into the organ or vessel (not shown) via an incision (not shown), and the proximal section 30a of the tube 30 protrudes perpendicular to the skin surface. For application of the plaster device, at least a part of the foil 5 is initially removed, and the flap 9 is swung aside to make room for the inserted tube 30, and the plaster device 1 is adhered to the skin with the tube extending from the incision. The centre of the support section 16 is thereby situated adjacent the through-opening 7 in the adhesive part 2 so as to support the proximal section 30a of the inserted bent tube close to the incision site as seen best in FIG. 3.

The second jaw 13 is pivoted apart from the first jaw 12 to open the gab between the first and second jaws 12,13 to provide room for the distal section 30b of the inserted bent tube as shown in FIG. 3.

In FIG. 4 the second jaw 13 is pivoted back towards the first jaw 12 to fixate and protect between the jaws 12,13 the retracted distal section 30b of the tube 30. The foamed material of the support part 11 is resilient so that, when the tube is placed between the two jaws which are pressed gently against each other, a bore or groove for accommodating the distal section 30b of the tube 30 is automatically formed. The wall of the bore holds the tube in place due to frictional and slight compressive forces. The resilient material ensures that the tube is not overcompressed.

It is preferred that at least the protrusions 18,20a,20b is coated with a friction lining. Alternatively the material of the support part 2 is chosen to have a high coefficient of friction towards the tube material. Suitable materials for the friction include but are not limited to natural and synthetic rubbers.

In FIG. 4 the first cover part 26 is shown to partly cover the support part 11. The VELCRO® hook and loop fastener sheet is made to couple together with the second cover part 22 and the third cover part 23a,23b to completely enclose the support part, as seen in FIG. 5, and hold the jaws in a clamping position around the distal section 30b of the tube 30.

It is preferred that the area of the adhesive part exceeds the base area of the support part, and that the adhesive part's through-opening for the tube is located at a distance from the perimeter of the adhesive part in order to provide room for the joining of the cover parts.

These demands are also met in the second embodiment 31 shown in the exploded view of FIG. 6.

The plaster device 31 includes an adhesive part 32 having an upper side 33 partly covered with a soft woven or non-woven material 33 and an adherent lower side 44 coated with a skin-friendly adhesive. The adherent lower side 44 is protected by a releasable foil 35 composed of three separately releasable pieces of foil 35a,35b,35c, having respective protruding foil finger tabs 35a',35a'',35b',35c'. The foils 35a,35b, 35c are removed just before the plaster device is attached to the skin surface (not shown) for use in a manner substantially similar to attachment procedure described for the first embodiment 1.

The soft material 33 has a central cut-out portion 36 defining a cavity sufficiently large to accommodate at least a section 37 of a first VELCRO® hook and fastener cover part 38 and the second VELCRO® hook and loop fastener cover parts 39,40a,40b. The section 37, and the second VELCRO® hook and loop fastener cover parts 39,40a,40b are joined to the upper side 33 of the cut-out portion 36, by e.g. gluing, as seen best in FIG. 7.

The plaster device further 31 comprise a support part 41, a third cover part 42 and a retainer plate 43.

A slit 44 extends from the perimeter of the adhesive part 32 a distance into the adhesive part 32 and divides out a first 45 and a second 46 access flap. Upon application of the plaster device 31 the foil 35 is removed, the access flaps 45,46 is lifted aside, the bottom 47 of the slit 44 is located at the incision site adjacent the inserted tube 30, and the lower side 34 of the adhesive part 32 is adhered to the skin of the patient.

Other geometries of the bottom 47 of the slit 44, such as e.g. circular holes, are within the scope of the present invention.

The support part 41 is substantially U-shaped and comprises first 48 and second 49 oppositely facing jaws for, in between them, taking hold of at least a section of the bent tube 30, said jaws 48,49 are interconnected at oppositely facing first ends 50,51, respectively, by a U-shaped support section 52. The parallel legs 50,51 of the U-shaped support section 52 are also the respective first ends 50,51 of the respective jaws 48,49. The bottom 53 of the U-shaped support section 52 is arranged adjacent to the bottom 47 of the slit 44 extending into the adhesive part 2.

The inside wall 54 of the first jaw 48 is formed with a protruding portion 55, which has an inside wall 59 which is coated with an adhesive means. The adhesive means is protected be means of a foil strip 56 until final use with an inserted tube. The second jaw 49 has a protruding breast 57 which, in the closed position of the jaws, rests on the shoulder 58 of the protruding portion 55 of the second jaw 49. The tube, which is accommodated between the jaws 48,49 for fixation, is gently stuck in the adhesive means of the inside wall 54 of the first jaw 48.

The first jaw 48 and the support section 52 of the support part 41 is permanently joined to the adhesive part 32 via the inserted section 37 of the first cover part 38 permanently joined to the cut-out section 37. Permanently joining of the parts can be made using an appropriate glue means. The second jaw 49 pivots freely on the support section 52 at the first end 51.

A freely moving portion 60 of the first cover parts is designed with a first 61 and a second flap 62 for coupling together with the second cover part 39 and surrounding the bend section of the tube. The freely moving portion 60 further has a third flap 63 opposite the first 61 and second 62 flaps for coupling together with the second cover part 40, said third flap 63 is designed with a protruding detachment flap 64 to be grasped between two fingers for uncoupling the first cover part 38 from the second cover parts 39,40. Opposite the section 37 the freely moving portion 60 of the first cover part 38 has a fourth flap 65 for coupling together with the third cover part 42 when the first cover part 38 is folded in over the support part 41.

Accordingly, as seen in FIG. 8, the third cover part 42 is joined to the top face and the outer face of the first jaw 48. The third cover part 42 is also joined to the soft material 33 on top of the adhesive part 32 and extends a small distance in over the soft material 33 adjacent the first jaw 48 to allow for secure coupling with the fourth flap 65.

A retainer plate 43 of a relatively rigid material such as a rigid plastic material or non-absorbent laminated cardboard is partly joined to the upper face of the support part 41. The retainer plate 43 can have any desired geometry meeting the demands for retaining of the tube between the jaws 48,49.

The elements shown in FIG. 6 are combined to the plaster device 31 as shown in FIG. 7-10.

In FIG. 7 the protective foil 35 is shown partly detached from the adhesive part 32 and in FIG. 8-10 the foil 35 is entirely removed.

For illustrative purposes a tube 30 is shown traversing the adhesive part 32 via the slit 44. The tube 30 is inserted into the organ or vessel (not shown) via an incision (not shown), and the proximal section 30a of the tube 30 protrudes perpendicular to the skin surface. For application of the plaster device 31, the foil 35 is initially removed, and the access flaps 45,46 is swung aside to make room for the inserted tube 30. The plaster device 31 is adhered to the skin with the tube 30 extending from the incision. The centre of the support section 52 is thereby situated to support the proximal section 30a of the inserted bent tube 30 close to the incision site.

As seen in FIG. 8 the second jaw 49 is pivoted apart from the fixated first jaw 48 to open the gab between the first 48 and second 49 jaws and to provide room for the distal section 30b of the inserted bent tube 30.

In FIG. 9 the distal section 30b of the tube 30 is bent to be placed between the first 48 and second 49 jaws.

The retainer plate 43 consist of a L-shaped part 43a,43b and a U-shaped part 43b,43c. The foot 43a extends via substantially right angle into the leg 43b. Said leg 43a is identical to one of the legs 43b,43c of the U-shaped part of the retainer plate 43. The leg 43b of the retainer plate 43 is joined to the upper face of the first jaw 48. A portion of the foot 43a and the U-shaped part 43c is left free to move to allow the second jaw 49 to pivot freely.

For final fixation of the tube in relation to the plaster device 31 the foil strip 56 is removed and the distal section 30b of the tube 30 is bent in over the foot 43a, which rests on top of the support section 52. The distal section 30b is the guided in under the U-shaped part 43b,43c of the retainer plate 43 and stuck on the inside wall 59 of the protruding portion 58 of the first jaw 48 of the support part 41.

The second jaw 49 is pivoted back towards the first jaw 48 to fixate and protect between the jaws 48,39 the retracted distal section 30b of the tube 30. The resilient material of the support part ensures that the tube is not compressed and the foot 43a of the retainer plate 43 contribute in avoiding overcompression of the support section 52. As result of the foot 43a of the retainer plate, the support sections the support capability is highly improved and maintained during the entire use period of the plaster device 31.

In FIG. 10 the first cover part 38 is shown to almost entirely cover the support part 41. The flaps 61,62,63,64 of the VELCRO® hook and loop fastener sheet 38 is made to couple together with the second cover parts 39,40 and the third cover part 42 to enclose the support part 41 and the distal section of the bent tube 30b and to hold the jaws 48,49 clamped around the tube 30.

The VELCRO® hook and loop fastener parts are very easy to disengage. In this second embodiment uncoupling or disengagement of the cover parts take place stepwise. As a result, the detachment force is distributed over a number of different points so that when the support part is uncovered for inspection of the tube the adhesive part will not detach from the skin surface. Hence, it is possible to inspect the tube and the incision site in an easy manner.

Preferably the VELCRO® hook and loop fastener sheet of the first cover part has a smooth outside so that the plaster device not does catch the patient's clothes or other surrounding, protruding elements.

In the drawing both the support part and the adhesive part are of substantially rectangular outlines just for illustrative purposes.

The invention claimed is:

1. A plaster device for fixating a length of a medical tube in relation to a skin surface of an individual having the tube inserted into a body part via an access opening, the plaster device comprising an adhesive part having an upper side, an adherent lower side for attaching the plaster device to the skin, an opening for receiving the tube, and a support part provided on the upper side of the adhesive part adjacent the opening, the support part positioned to accommodate an inserted tube having a portion that passes through the opening and a bent length engaged with the support part, wherein the support part is partly joined to the adhesive part and comprises first and second oppositely facing, elongate jaws configured for, in between them, holding at least part of the bent length of the inserted tube, with the jaws being interconnected at oppositely facing first ends by a support section arranged adjacent to the opening in the adhesive part and extending to oppositely facing second ends at an angle from each other to provide room for holding the tube, and with at least one of the jaws being pivotably connected to an end of the support section and being movable relative to the other, with the support section of the jaws positioned adjacent to the access opening and the seconds ends of the jaws positioned distal to the access opening.

2. The plaster device according to claim 1, wherein the plaster device further comprises a cover including a first cover part arranged for coupling together with either a second cover part attached to at least a section of the upper side of the adhesive part or for coupling to the adhesive part itself.

3. The plaster device according to claim 2, wherein a third cover part of a VELCRO® strip is provided on at least a part of a top face or a part of an outer side face of the support part for engaging with the first cover part.

4. The plaster device according to claim 3, wherein the first, the second or the third cover part together with the first and second jaws constitute a means for fastening the bent length of the tube.

5. The plaster device according to claim 2, wherein the first cover part is an at least partly detachable textile sheet of a VELCRO® strip of an area sufficiently large to cover at least the support part of the plaster device in the position of use, and the second cover part is an annular VELCRO® strip attached to the upper side of the adhesive part along the perimeter of the adhesive part, or the second cover part is at least one VELCRO® strip attached to the upper side of the adhesive part adjacent at least a part of the support part.

6. The plaster device according to claim 2, wherein a section of the first cover part is inserted between the upper side of the adhesive part and the support part and is secured permanently to both parts.

7. The plaster device according to claim 2, wherein the first cover part is provided with flaps for engaging the second or third cover parts.

8. The plaster device according to claim 1, wherein the jaws have substantially complementarily shaped, oppositely facing inside walls that include complementarily shaped protrusions configured to accommodate the bent tube between the jaws in frictional, non-displaceable engagement without compressing the tube.

9. The plaster device according to claim 8, wherein at least one of the inside walls is provided with an adhesive optionally covered by an detachable protective strip.

10. The plaster device according to claim 1, wherein at least the support section is permanently joined to the upper side of the adhesive part.

11. The plaster device according to claim 1, wherein the plaster device comprises a retainer plate for holding the bent section of the inserted tube in the space between the jaws, with the retainer plate being secured to the upper side of the support part.

12. The plaster device according to claim 1, wherein the adhesive part has a slit extending from the outer perimeter of the adhesive part to the opening.

13. The plaster device according to claim 1, which further comprises a pad which is inserted between the adhesive part and the support section adjacent the opening in the adhesive part, wherein the opening has an area which allows the pad to have direct access to a skin area adjacent or around the opening in the body part.

14. The plaster device according to claim 1, wherein at least the pad comprises at least one of the substances selected from the group including an absorbent agent, a bactericide, a fungicide or a medicament.

15. The plaster device according to claim 1, wherein the adherent lower side of the adhesive part is protected by a releasable protecting foil.

* * * * *